United States Patent
Mewes

(10) Patent No.: US 10,434,645 B2
(45) Date of Patent: Oct. 8, 2019

(54) MEDICAL ROBOT AND OPERATION THEREOF

(71) Applicant: Philip Mewes, Nürnberg (DE)

(72) Inventor: Philip Mewes, Nürnberg (DE)

(73) Assignee: Siemens Aktiengesellschaft, München (DE)

(*) Notice: Subject to any disclaimer, the term of this patent is extended or adjusted under 35 U.S.C. 154(b) by 660 days.

(21) Appl. No.: 14/809,347

(22) Filed: Jul. 27, 2015

(65) Prior Publication Data

US 2016/0030116 A1 Feb. 4, 2016

(30) Foreign Application Priority Data

Jul. 29, 2014 (DE) .................. 10 2014 214 861

(51) Int. Cl.
*B25J 9/16* (2006.01)
*A61B 34/37* (2016.01)
(Continued)

(52) U.S. Cl.
CPC ............ *B25J 9/1615* (2013.01); *A61B 34/30* (2016.02); *A61B 34/35* (2016.02); *A61B 34/37* (2016.02); *B25J 9/1664* (2013.01); *A61B 2034/305* (2016.02); *G05B 2219/39209* (2013.01); *G05B 2219/40074* (2013.01); *G05B 2219/40456* (2013.01); *G05B 2219/40457* (2013.01); *G05B 2219/40512* (2013.01);
(Continued)

(58) Field of Classification Search
CPC ... A61B 2034/305; A61B 34/30; A61B 34/37; A61B 34/10; A61B 2034/107; B25J 9/1664; B25J 9/1666

USPC .......................................................... 606/130
See application file for complete search history.

(56) References Cited

U.S. PATENT DOCUMENTS 9,393,692 B1* 7/2016 Theobald ............... B25J 9/1666
2008/0082110 A1 4/2008 Rodriguez Ponce
(Continued)

FOREIGN PATENT DOCUMENTS

EP 1905377 A1 4/2008
WO WO2014001948 A2 1/2014

OTHER PUBLICATIONS

"Industrial robot", in: http://en.wikipedia.org/wiki/Industrial_robot, pp. 1-9, 2013.
(Continued)

*Primary Examiner* — Diane D Yabut
*Assistant Examiner* — Majid Jamialahmadi
(74) *Attorney, Agent, or Firm* — Lempia Summerfield Katz LLC

(57) ABSTRACT

The embodiments relate to a method for operating a medical robotic device with an end effector for performing a diagnostic and/or therapeutic measure, involving predetermining at least one position to be reached by the end effector, evaluating at least two movement sequences of the medical robotic device, by which the end effector reaches the respectively predetermined at least one position, using an optimization criterion to select the movement sequence with the best evaluation result as the optimum movement sequence and implementing the optimum movement sequence, so that the respective predetermined position is reached by the end effector, in order to improve the reaching of the predetermined position.

15 Claims, 1 Drawing Sheet

(51) Int. Cl.
*A61B 34/30* (2016.01)
*A61B 34/35* (2016.01)

(52) U.S. Cl.
CPC ... *G05B 2219/45118* (2013.01); *Y10S 901/02* (2013.01); *Y10S 901/30* (2013.01); *Y10S 901/46* (2013.01)

(56) References Cited

U.S. PATENT DOCUMENTS

| | | | | |
|---|---|---|---|---|
| 2009/0003975 | A1* | 1/2009 | Kuduvalli | A61N 5/1049 414/146 |
| 2011/0035053 | A1* | 2/2011 | Guochunxu | B25J 9/1664 700/255 |
| 2011/0208034 | A1* | 8/2011 | Heid | G01S 13/06 600/407 |
| 2013/0304084 | A1* | 11/2013 | Beira | A61B 19/2203 606/130 |
| 2014/0371762 | A1* | 12/2014 | Farritor | A61B 19/2203 606/130 |
| 2015/0190204 | A1 | 7/2015 | Popovi | |

OTHER PUBLICATIONS

German Office Action for related German Application No. 10 2014 214 861.8, dated Apr. 12, 2015 with English Translation.
Robotische Bewegungskompensation durch interne Drehmomentsensorik, 2014 with English Translation.
Saùl Tovar-Arriaga, et.al.: "A Fully Sensorized Cooperative Robotic System for Surgical Interventions," in: Sensors, vol. 12, pp. 9423-9447, 09. Jul. 2012.
The American National Standard for Industrial Robot Systems—Safety Requirements, ANSI/RIA R15.06-1999.

* cited by examiner

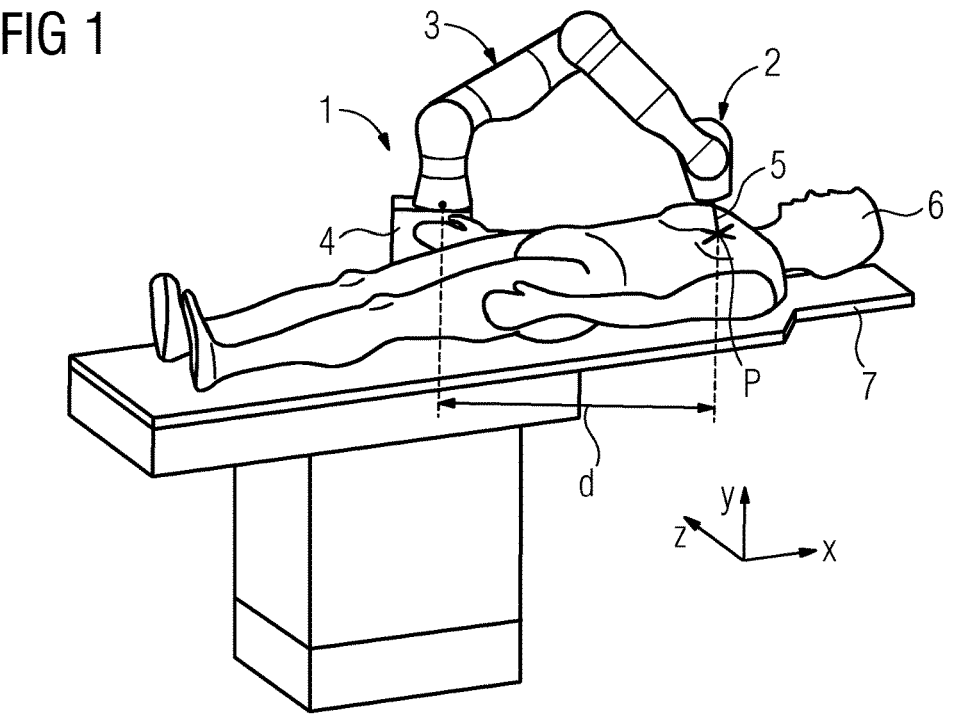
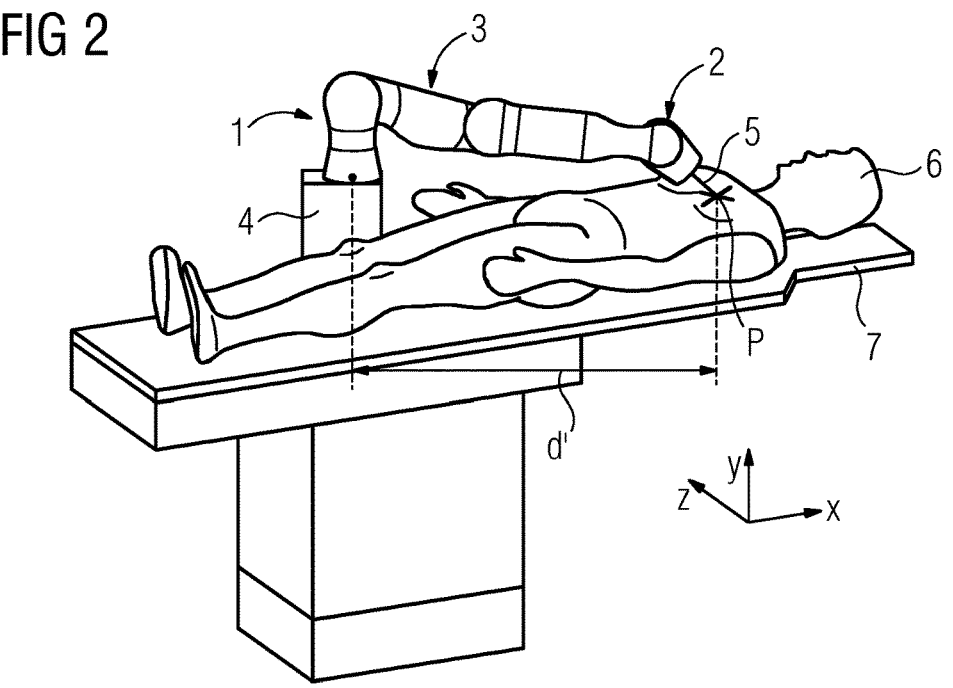

MEDICAL ROBOT AND OPERATION THEREOF

CROSS-REFERENCE TO RELATED APPLICATIONS

This application claims the benefit of DE 10 2014 214 861.8, filed on Jul. 29, 2014, which is hereby incorporated by reference in its entirety.

TECHNICAL FIELD

The embodiments relate to a method for operating a medical robotic device with an end effector for performing a diagnostic and/or therapeutic measure. The embodiments also relate to a medical robotic device with an end effector for performing a diagnostic and/or therapeutic measure and with a control unit for implementing a movement sequence of the device.

BACKGROUND

Stringent requirements govern the accuracy of medical robotic devices or, in other words, devices that are able automatically to perform a movement or automatically to prevent defined movements of the device during an operating intervention. Accuracy here refers to how precisely a device may approach a predetermined position and/or may take up the position. If the absolute position of the device is measured and compared with the desired position, any difference is a measure of the accuracy. The accuracy of a medical robotic device may be a function of the position the device takes up and a speed with which the position is taken up. In the case of multiaxial medical robotic devices with many degrees of freedom, (in other words many movement options that are independent of one another), the accuracy of the device is a function of the kinematic configuration of the device or its axes. In principle, devices with a large number of degrees of freedom are also advantageous in medical applications, as they allow a high level of flexibility to be achieved with regard to positional accuracy, (in other words in respect of the space problem in many operating scenarios).

With multiaxial devices, in extreme instances referred to as singularities, very significant inaccuracies and even behavior that may no longer be predicted may result. A singularity is defined here in accordance with the ANSI safety standard ANSI/RIA R15.06-1999 as a condition that may be ascribed to a collinear alignment of two or more axes of a robot and results in unpredictable movement and movement speeds of the robot.

SUMMARY AND DESCRIPTION

The scope of the present invention is defined solely by the appended claims and is not affected to any degree by the statements within this summary. The present embodiments may obviate one or more of the drawbacks or limitations in the related art.

It is the object of the present embodiments to achieve improved positioning for a medical robotic device.

A method for operating a medical robotic device with an end effector for performing a diagnostic and/or therapeutic measure includes a series of acts in order to achieve improved positioning An end effector here, as may be the case in robotics, refers to a last element of a chain of adjoining elements that may be moved relative to one another by control commands, of a kinematic chain, of the medical robotic device. In one act, at least one position to be reached by the end effector is predetermined. A position may in principle also include a predetermined orientation of the end effector in this position. A position may also include a sequence of subpositions to be reached one after the other in time by the end effector, it being possible for the subpositions in turn to also include an orientation, as is required for example for an abrasion performed by the end effector.

In a further act, there is an evaluation, using an optimization criterion, of at least two movement sequences of the medical robotic device, by which the end effector reaches the respectively predetermined at least one position. There may be a number of possible positions and/or trajectories for reaching the at least one position of the device that are available for performing a measure, for the same diagnostic and/or therapeutic measure. For example, a biopsy on a defined soft part organ may take place in various positions on the organ. One example of different trajectories or movement sequences and resulting different end configurations of the medical robotic device in an identical position is a drilling template that may be held in a defined predetermined position from different sides.

In a subsequent act, the movement sequence with the best evaluation result is appointed as the optimum movement sequence. In other words, the kinematic movement plan of the robot is selected so that on the one hand the set medical treatment parameters are satisfied, (e.g., an organ to be reached is reached), and on the other hand also the kinematic movement sequence of the medical robotic device is optimized based on the optimization criterion, (e.g., the organ to be reached is reached in a kinematically optimum manner). Such optimization therefore takes into account the movement sequence of the robot from a start position to the final target position.

In an additional act, the optimum movement sequence is implemented, so that the respective predetermined position and/or orientation is reached by the end effector. Thus, after implementation the device is in an optimized kinematic location or configuration or axis configuration. Implementation here may be active or passive. In other words, either the medical robotic device may perform the optimum movement sequence automatically or may be made to do so by an operator in what is known as "gravity mode", or a manual mode, taking account of what are known as "active constraints", (that is, taking into account predetermined basic conditions). In such a gravity mode with active constraints, the medical robotic device automatically restricts its capacity for movement by a user, (e.g., the device's degrees of freedom), according to the predetermined basic conditions so that the application of a force, (e.g., pushing or pulling), by an operator may only bring about a movement of the device and therefore of the end effector according to a movement sequence predetermined by the medical robotic device. The medical robotic device is therefore freely movable but defined axes and/or defined Cartesian degrees of freedom are restricted.

This has the advantage that it is possible to select an optimum movement sequence from a plurality of initially equal movement operations and geometric configurations of the medical robotic device, which all satisfy the medical purpose. This improves the positioning of the medical robotic device.

In one advantageous embodiment, the respectively predetermined positions are identical positions. This has the advantage that not only are different positions taken into account for the performance of an operation but different movement sequences may also be verified and therefore optimized for a single respective predetermined position.

In a particularly advantageous embodiment, the optimization criterion takes into account inaccuracies that are expected to occur during the different movement sequences due to the kinematic robotic properties of the medical robotic device. The expected inaccuracies here are the inaccuracies that are known to occur during the actual performance of a defined movement sequence. These may be estimated, for example, based on a model that the medical robotic device has per se or may be stored in a table. In particular, the movement sequence with the fewest expected inaccuracies may be selected as the optimum movement sequence. This has the advantage that the accuracy of a position reached by the end effector is increased. In other words, the positioning of the device is improved. As a consequence the corresponding diagnostic and/or therapeutic measure is performed with greater precision.

In a further embodiment, the medical robotic device is operated in a mode in which the medical robotic device automatically restricts its own capacity for movement and may only be moved manually by an operator according to movement sequences provided by the medical robotic device and this restricted capacity for movement is taken into account when evaluating the movement sequences. The device is therefore operated in the "gravity mode" described above taking account of "active constraints". Because of the so-called "active constraints" applied automatically by the medical robotic device the medical robotic device, (e.g., the end effector), may therefore only be moved in a direction defined by the medical robotic device. The evaluation of the different movement sequences is particularly advantageous here as medical robotic devices are particularly prone to singularities during the technical implementation of the active constraints.

In particular, it is possible here for the active constraints that leave the device in the most stable state possible, (in other words, avoiding states in which major inaccuracies or even singularities are known to occur easily), to be targeted according to the optimization criterion. The movement spaces of the medical robotic device in which the device may be moved in a particularly accurate and stable manner despite any active constraints present are made available. This has the advantage that human awareness and direct feedback to the operator may be combined with the greatest possible precision of the medical robotic device. For example, a biopsy needle may be positioned and aligned in such a manner that the needle pierces the desired biopsy point when advanced in the direction of the needle tip. The advance is then not executed by motorized movement of the robot however; instead, the active constraints are set in such a manner that the medical robotic device, or in this instance the end effector with the biopsy needle, may only be moved manually by an operator in the direction of the needle tip. As the operator therefore knows the force with which the needle tip is moved, resulting haptic and/or visual feedback from the movement of the needle tip is interpreted correctly by the operator.

In a further embodiment, the medical robotic device has an overdefined kinematic, e.g., with at least seven degrees of freedom. A device with an overdefined kinematic has very many different kinematic configurations that may all reach the same position and/or orientation but by way of different movement sequences and therefore with differing accuracy and stability. The medical robotic device with an overdefined kinematic may therefore reach a predetermined position using different articulations or different movement combinations about the articulations. This has the advantage that a particularly large number of movement sequences may be evaluated and positioning may therefore be improved particularly significantly.

In a further advantageous embodiment, at least one additional degree of freedom for the medical robotic device results from a movement of the medical robotic device as a whole relative to an environment of the device, e.g., relative to a body to be operated on, on which an operating intervention is to be performed with the aid of the medical robotic device. In particular, during such movement the end effector and further components of a kinematic chain associated with the end effector may remain unmoved relative to one another. Provision is made here in particular for movement of the medical robotic device along a securing rail to which the medical robotic device may be fixed in different positions. The securing rail is attached in particular to an operating table. Provision may also be made here for movement of a movable trolley and/or a ceiling mounting or similar securing options on which the medical robotic device is arranged, in order to increase the number of degrees of freedom. After movement of the device as a whole it is recalibrated or reset to a coordinates system used if the movement itself does not take place in a precisely defined, calibrated manner. This has the advantage that alternative movement operations may also be considered for devices that otherwise would not have sufficient degrees of freedom for the alternative movement operation, particularly in a kinematic chain. Thus for example already existing devices may achieve better positioning than with a former operating mode or such improved positioning may also be achieved with more favorable medical robotic devices, which have fewer degrees of freedom.

In one embodiment, at least one additional degree of freedom for the medical robotic device results from a movement of an operating table, e.g., a part of an operating table configured as a support surface, relative to the device. Here, a body to be operated on, on which an operating intervention is to be performed with the aid of the medical robotic device, is present on the operating table, so that movement of the operating table results in a movement of the body to be operated on relative to the medical robotic device. This has the advantage that the capacity for movement of the operating table, which may be given, is used for improved positioning of the medical robotic device. No additional components such as a securing rail or the like for example are required here so improved positioning may be achieved in a particularly simple manner. If the operating table may be moved not only manually but also automatically, in some instances it is superfluous to reset the medical robotic device and the additional degree of freedom achieved by moving the operating table may be taken into account particularly easily when evaluating the different movement operations.

In a further embodiment, the end configurations are identified according to the optimization criterion, wherein the end configurations refer to the movement operations that result in the end configurations of the medical robotic device in which sensors in the device respond more significantly to external forces expected during the performance of the diagnostic and/or therapeutic measure and acting on the end effector. The sensors may be torque sensors. A movement operation is thus chosen, at the end of which the device is in a configuration in which a force acting on the device, (e.g., on the end effector), may be detected particularly readily by way of the sensors. This is of particular interest for forces that are likely to occur as a result of the diagnostic and/or therapeutic measure to be performed, for example the resistance expected when taking a biopsy from a soft part tissue. This has the advantage that additional positioning information is available. For example, a resistance force that is greater or less than expected when taking a biopsy indicates that the positioning is perhaps inaccurate so corrective measures may be taken to improve positioning.

Provision may be made in particular here for positions and/or orientations of the end effector to be identified according to the optimization criterion, in which sensors in the device respond more significantly to the external forces. The sensors here may again in particular be torque sensors. This has the advantage that the external forces may be detected particularly accurately by way of the sensors as not only is the end configuration of the medical robotic device as a whole, for example, the length of a lever and the orientation of the lever relative to a vector of an expected external force, taken into account but also the position of the end effector or its orientation relative to the force. The end effector is thus positioned in a specific position and/or orientation relative to the expected direction of the forces acting on it. This has the advantage that it is particularly easy for the sensor system of the medical robotic device to measure the forces occurring during the course of the therapeutic and/or diagnostic measure in this manner.

If the optimization criterion takes into account different aspects of the movement operations, the different individual aspects are in particular weighted according to predetermined weighting factors. This has the advantage that evaluation of the different movement operations produces unique results.

The embodiments also relate to a medical robotic device with an end effector for performing a diagnostic and/or therapeutic measure and with a control unit for implementing a movement sequence of the device, which is designed, for at least one predetermined position to be reached by the end effector, to use an optimization criterion to perform an evaluation of at least two movement sequences of the medical robotic device, by which the end effector reaches the respectively predetermined at least one position. The control unit is further designed to select and implement the movement sequence with the best evaluation result. Implementation here may be active or passive, as described above.

Features and advantages of the embodiments of the method also apply to the apparatus.

BRIEF DESCRIPTION OF THE DRAWINGS

FIG. 1 depicts a schematic diagram of an example of a medical robotic device, which has reached a position to be reached with a first movement sequence.

FIG. 2 depicts a schematic diagram of the scenario from FIG. 1 after an exemplary embodiment of the proposed method has been performed.

Identical elements or those with identical function are depicted with identical reference characters in the figures.

DETAILED DESCRIPTION

FIG. 1 depicts a schematic diagram of a medical robotic device, which has reached a position to be reached with a first movement sequence. FIG. 1 depicts a medical robotic device 1, which has an end effector 2 for performing a diagnostic and/or therapeutic measure. In this example, the end effector 2 is arranged by way of a kinematic chain 3, in the present instance including five elements that may be positioned next to one another and moved in relation to one another on a base unit 4 of the medical robotic device 1. In the illustrated example, the end effector 2 has a biopsy needle 5, which is positioned at a position P to be reached by the end effector 2.

In the present instance, the position P is located on a body 6 to be operated on, which is lying on an operating table 7. The operating table 7 here extends mainly in an x direction, along which the length of the body 6 to be operated on, in the present instance a human patient, lies. The distance d between the base unit 4 of the medical robotic device 1 and the position P in the present instance is short compared with the length of the kinematic chain 3, so that the medical robotic device 1 or its kinematic chain 3 describes an arc with a number of angles in the illustrated configuration of the device 1 or the kinematic chain 3. In the present example, it is thus on the one hand only possible with difficulty to measure respiratory movements of the patient, which produce a rising and falling of the ribcage in the y direction, using sensors in the medical robotic device 1 or in this example in articulations 8 of the kinematic chain 3, as the orientation of the elements of the kinematic chain 3 has major components parallel to the movement direction. Thus, sensors in the articulations 8 of the kinematic chain may only record a torque with difficulty. Also, in the illustrated example, the setting of the various angles in the kinematic chain 3 is associated with major inaccuracies, so the end effector 2 causes the position P to be subject to an inaccuracy that may be reduced by improved positioning.

FIG. 2 depicts the scenario from FIG. 1 after an embodiment of the proposed method has been performed. Different movement sequences of the medical robotic device 1, which result in different configurations of the medical robotic device 1, (e.g., different configurations of the kinematic chain 3 and of the end effector 2), have been evaluated here. Evaluation in the present instance takes place on the basis of an optimization criterion, which on the one hand takes into account inaccuracies occurring in the selected movement sequence and on the other hand may be end configurations, which allow easier measuring of in the present instance torques acting on the medical robotic device 1 or the end effector 2 in the resulting end position. In this example, forces occurring in the y direction due to the respiratory movement are to be expected. Therefore, in the present instance, the orientation of the end effector 3 in the end position, here with the biopsy needle 5, has been taken account during the evaluation. The end configuration resulting from the movement sequence with the best movement result is depicted in the present instance.

As depicted in FIG. 1, the identical position P in the body 6 to be operated on is reached by the end effector 2. The base unit 4 of the medical robotic device 1 has been displaced, in this instance along the x axis, so that the distance d' between the position P and the base unit 4 has changed, in this instance increased, compared with the end configuration of the medical robotic device 1 depicted in FIG. 1. This provides that the orientation of the elements of the kinematic chain 3 has major components perpendicular to the movement direction, therefore being at a favorable angle to be able to measure the expected forces, (e.g., torques), by way of sensors, (e.g., torque sensors in the articulations 8).

The same advantageous end constellation may alternatively also be achieved by moving the operating table 7. This moves the body 6 to be operated on relative to the base unit 4 of the medical robotic device 1, which is equivalent to the displacement of the base unit 4 of the medical robotic device 1 relative to the operating table 7 holding the body 6 to be operated on as performed in FIG. 2.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical robotic device comprising a kinematic chain and an end effector positioned at an end of the kinematic chain, wherein the medical robotic device is configured to perform a diagnostic measure, a therapeutic measure, or diagnostic and therapeutic measures, the method comprising:
predetermining at least one position to be reached by the end effector;
evaluating at least two movement sequences of the medical robotic device using an optimization criterion, by which the end effector reaches the respectively predetermined position, wherein the at least two movement sequences comprise different movement sequences having different configurations of the kinematic chain with different accuracies while having a same predetermined position of the end effector, wherein the respective accuracy of a movement sequence of the at least two movement sequences is a function of a position the medical robotic device takes up and a speed with which the position is taken up, and wherein the optimization criterion takes into account inaccuracies expected to occur during different movement sequences due to kinematic robotic properties of the medical robotic device;
selecting the movement sequence of the at least two movement sequences with a best evaluation result as an optimum movement sequence, wherein the optimum movement sequence is the movement sequence with fewest expected inaccuracies due to the kinematic robotic properties of the kinematic chain of the medical robotic device; and
implementing the optimum movement sequence, so that the respective predetermined position is reached by the end effector.

2. The method as claimed in claim 1, wherein the medical robotic device is operated in a mode in which the medical robotic device automatically restricts a capacity for movement of the medical robotic device and is configured only to be moved manually by an operator according to movement sequences provided, wherein the restricted capacity for movement is taken into account when evaluating the movement sequences.

3. The method as claimed in claim 1, wherein the medical robotic device has an overdefined kinematic, wherein the overdefined kinematic comprises a plurality of different articulations of the kinematic chain with the end effector in the same predetermined position.

4. The method as claimed in claim 3, wherein the overdefined kinematic comprises at least seven degrees of freedom.

5. The method as claimed in claim 4, wherein at least one additional degree of freedom for the medical robotic device results from a movement of the medical robotic device as a whole relative to an environment of the medical robotic device.

6. The method as claimed in claim 5, wherein the end effector and further components of the kinematic chain associated with the end effector are configured to remain unmoved relative to one another during movement of the medical robotic device along a securing rail.

7. The method as claimed in claim 4, wherein at least one additional degree of freedom for the medical robotic device results from a movement of an operating table relative to the medical robotic device.

8. The method as claimed in claim 1, wherein at least one degree of freedom for the medical robotic device results from a movement of the medical robotic device as a whole relative to an environment of the medical robotic device.

9. The method as claimed in claim 8, wherein at least one additional degree of freedom for the medical robotic device results from a movement of an operating table relative to the medical robotic device.

10. The method as claimed in claim 1, wherein at least one degree of freedom for the medical robotic device results from a movement of an operating table relative to the medical robotic device.

11. The method as claimed in claim 1,
wherein the medical robotic device comprises at least one sensor, and
wherein end configurations are selected according to the optimization criterion, in which the at least one sensor in the medical robotic device responds more significantly to external forces expected to act on the end effector during the performance of the diagnostic measure, the therapeutic measure, or the diagnostic and the therapeutic measures.

12. The method as claimed in claim 11, wherein the at least one sensor is a torque sensor.

13. The method as claimed in claim 11, wherein the positions, orientations, or the positions and the orientations of the end effector, in which the at least one sensor in the medical robotic device responds more significantly to the external forces, are preferred according to the optimization criterion.

14. The method as claimed in claim 13, wherein the at least one sensor is a torque sensor.

15. The method as claimed in claim 1, further comprising:
detecting an external force by a torque sensor of the medical robotic device,
wherein the optimum movement sequence is implemented such that the predetermined position of the end effector is positioned relative to the expected direction of the external force.

* * * * *